(12) United States Patent
Bishop et al.

(10) Patent No.: US 8,100,605 B2
(45) Date of Patent: Jan. 24, 2012

(54) ZEOLITE COMPOSITE MATERIALS FOR WASTE ODOR CONTROL

(75) Inventors: Karl Duncan Bishop, Orono, ME (US);
Michael A. Bilodeau, Brewer, ME (US);
Susan G. Mackay, Veazie, ME (US);
Douglas M. Ruthven, Old Town, ME (US)

(73) Assignee: University of Maine System Board of Trustees, Bangor, ME (US)

( * ) Notice: Subject to any disclaimer, the term of this patent is extended or adjusted under 35 U.S.C. 154(b) by 564 days.

(21) Appl. No.: 12/124,912

(22) Filed: May 21, 2008

(65) Prior Publication Data

US 2008/0293614 A1 Nov. 27, 2008

Related U.S. Application Data

(60) Provisional application No. 60/931,044, filed on May 21, 2007.

(51) Int. Cl.
*B09C 1/00* (2006.01)
(52) U.S. Cl. .............................. 405/129.9; 405/129.95
(58) Field of Classification Search ............... 405/129.9, 405/129.95
See application file for complete search history.

(56) References Cited

U.S. PATENT DOCUMENTS

| | | | |
|---|---|---|---|
| 5,116,793 A * | 5/1992 | Chao et al. ...................... 502/68 |
| 5,416,133 A | 5/1995 | Garcia et al. |
| 5,525,296 A | 6/1996 | Hollinger, Jr. |
| 5,556,699 A * | 9/1996 | Niira et al. ..................... 428/323 |
| 5,565,503 A | 10/1996 | Garcia et al. |
| 5,620,281 A | 4/1997 | Lammers et al. |
| 5,736,032 A | 4/1998 | Cox et al. |
| H1732 H | 6/1998 | Johnson |
| H001732 H * | 6/1998 | Johnson ........................ 428/68 |
| 5,981,052 A | 11/1999 | Sugiyama |
| 6,068,681 A | 5/2000 | Bourguignon |
| 6,197,398 B1 * | 3/2001 | Mathieson ..................... 428/57 |
| 6,372,333 B1 | 4/2002 | Sugiyama et al. |
| 6,435,770 B1 | 8/2002 | Shi |
| 6,524,667 B1 | 2/2003 | Colgan |
| 6,558,079 B1 * | 5/2003 | Kozak et al. ............. 405/129.15 |
| 6,558,080 B2 | 5/2003 | Kozak |
| 6,558,548 B2 * | 5/2003 | Svirklys et al. ............... 210/603 |

(Continued)

FOREIGN PATENT DOCUMENTS

GB 2288598 A * 10/1995

(Continued)

OTHER PUBLICATIONS

International Search Report and Written Opinion, International Application No. PCT/US2008/064337, University of Maine System Board of Trustees, Jan. 9, 2009, 9 pages.

(Continued)

*Primary Examiner* — John Kreck
(74) *Attorney, Agent, or Firm* — Wilmer Cutler Pickering Hale and Dorr LLP

(57) ABSTRACT

A composite material for environmental odor control is useful in controlling odors from waste, for example, as an alternative daily cover for landfills and in composting applications. The composite material includes a fiber web and a zeolite containing metals to promote absorption of odorous gas.

17 Claims, 8 Drawing Sheets

U.S. PATENT DOCUMENTS

| | | | |
|---|---|---|---|
| 6,806,298 | B1 | 10/2004 | Nachtman et al. |
| 7,090,916 | B2 | 8/2006 | Aamodt et al. |
| 7,175,741 | B2 | 2/2007 | West et al. |
| 2002/0018865 | A1 | 2/2002 | Blinka et al. |
| 2004/0171318 | A1 | 9/2004 | Rashed |
| 2004/0213755 | A1 | 10/2004 | Hochwalt et al. |
| 2005/0027081 | A1* | 2/2005 | Okushita et al. ............ 525/419 |
| 2005/0054252 | A1 | 3/2005 | Baciu et al. |
| 2005/0084334 | A1 | 4/2005 | Shi et al. |
| 2005/0113771 | A1 | 5/2005 | MacDonald et al. |
| 2005/0220542 | A1 | 10/2005 | Marsh et al. |
| 2006/0191655 | A1* | 8/2006 | Nunn et al. ................ 162/147 |
| 2008/0057134 | A1 | 3/2008 | Crudden |

FOREIGN PATENT DOCUMENTS

| | | | |
|---|---|---|---|
| WO | WO-9746193 | A1 | 12/1997 |
| WO | WO-9746196 | A1 | 12/1997 |

OTHER PUBLICATIONS

Cai et al., "Evaluation of Zeolite for Control of Odorants Emissions from Simulated Poultry Manure Storage", *J. Environ. Qual.* 36:184-193, 2007, 10 pages.

Dincer et al., "Chemical Characterization of Odorous Gases at a Landfill Site by Gas Chromatography-Mass Spectrometry", *J. Chromatog. A.* 1122:222-229, 2006, 8 pages.

Haughy, "Report: Landfill Alternative Daily Cover: Conserving Air Space and Reducing Landfill Operating Cost", *Waste Management Research*. 19:89-95, 2001, 8 pages.

Paraskaki et al., "Quantification of Landfill Emissions to Air: A case Study of the Ano Liosia Landfill Site in the Greater Athens Area", *Waste Management and Research* 23: 199-208, 2005, 11 pages.

Raven Industries, Dura-Skrim—http://www.ravenefd.com/pdf/DS8-12.pdf, 2 pages.

* cited by examiner

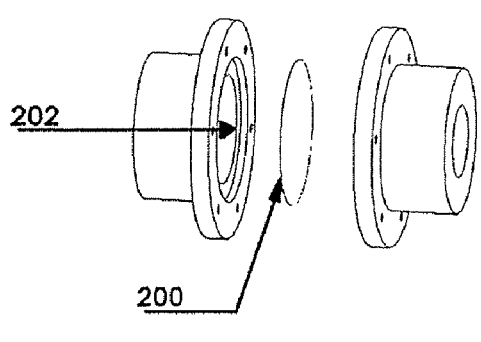 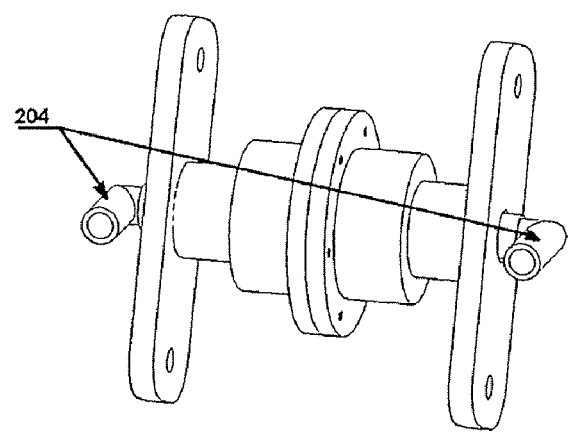
FIG. 2A  FIG. 2B
FIGURE 2

ZEOLITE COMPOSITE MATERIALS FOR WASTE ODOR CONTROL

RELATED APPLICATIONS

This application claims priority to U.S. Provisional Application No. 60/931,044 filed on May 21, 2007, which is incorporated herein by reference.

BACKGROUND

1. Technical Field

The present disclosure relates to environmental odor control technology. In particular, the disclosure relates to zeolite composite products for waste odor control applications, such as landfills and composting.

2. Summary of Related Art

Sanitary landfills are sources of hydrogen sulfide, greenhouse gases, and more than 100 non-methane organic compounds (NMOCs) of which over 30 are designated as hazardous air pollutants. A principle class of odorous compounds emitted from landfills is sulfur-based gases (Paraskaki et al., *Waste Management and Research* 23:199-208 (2005); Dincer et al., *J. Chromatog. A* 1122:222-229 (2006)). For example, hydrogen sulfide is a toxic gaseous compound that forms a primary component of emissions from solid waste sites. Landfill caps are used to control the emissions of such gases once the landfill is at maximum grade. However, prior to reaching the grade for capping, a landfill needs to have a daily cover applied.

Traditional daily covers for landfills consist of soil applied to the surface; however this is a labor intensive process which consumes valuable landfill space. Owners and operators of municipal solid waste landfills (MSWLF) typically are required to cover disposed solid waste with 30 cm of earthen material at the end of each day of operation. More frequent applications of earthen material may be necessary to control fire hazards, blowing litter, odors, insects, vectors, and rodents (Haughy, *Waste Management Research* 19:89-95 (2001); ASTM Standard Designation D6523, Standard Guide for Evaluation and Selection of Alternative Daily Covers (ADCs) for Sanitary Landfills (2005); Ohio EPA Guidance Document #0654, OAC Rule 3725-27-19 (Nov. 2, 2004)). It is also required that waste not be uncovered or exposed for more than 24 hours after unloading.

Other options or alternatives to the daily cover have been approved. Alternative Daily Covers, or ADC's, are primarily valued for their ability to conserve airspace by reducing the soil cover needed for landfills. ADCs fall into two major categories: tarps and spray-on materials. The various spray-on ADCs include foam, mulch, and slurries which harden after application. Each of these alternatives provides adequate cover while freeing up hundreds of cubic yards of space per ½ acre working face. The major cost savings for ADCs is realized by extending the life of the landfill; however, this can be offset by materials and application cost for the ADC.

Tarp or blanket ADCs can be reusable or nonreusable. Reusable types are commonly constructed of polypropylene or polyethylene and are deployed and weighted down for overnight use, then retracted each morning. Reusable blanket ADCs are designed to be puncture and tear resistant. Nonreusable ADCs are commonly composed of thin polypropylene, polyethylene, or polyvinyl chloride. Some nonreusable ADCs are thermally degradable and last from about 4 to 6 weeks. Other nonreusable ADCs are more resistant to degradation and are perforated so that the blanket ADC does not act as an impervious membrane. Tensile strength is also consideration in designing an ADC, although requirements can vary greatly and depend on the method of application and characteristics of the MSWLF. Reusable ADCs that are mechanically deployed and retracted typically are designed to be tough and durable. However, tensile strength is less important for a non-reusable ADC that is deployed and left in place.

There are two categories of spray ADCs, foams and slurries. Resin or soap commonly is mixed with water to create foam. Specialized spray equipment can then be utilized to apply the foam to the surface of the landfill. This forms a thin layer over the waste that does not harden. Spray application with no "shadowing" may require additional applications from various directions to ensure a thin, even layer. Foams do not need to be removed; they reduce to almost nothing as layers of waste are placed upon them. Slurry-based ADCs typically are created by mixing solid material with water and spraying the mixture on the working face of the landfill. Specialized hydro seeding equipment is typically necessary for application of the slurries. Spray ADCs have the advantage of limiting the loss of landfill volume by taking the place of 6 or more inches of soil as an odor control measure. Conserving space extends the life of the landfill, thereby making the landfill more cost effective. However, spray ADCs typically require the additional costs of leasing or purchasing specialized equipment and the maintenance of this equipment to apply the ADC.

In addition to landfills, waste and odor control issues are addressed in the context of composting by individual homeowners and larger scale organic waste producers, such as retail supermarket chains. In view of our society's rising environmental consciousness, a need exists for an alternative daily cover that is effective in the reduction of odors from landfills, composting facilities and other waste.

SUMMARY

The formulation and application of a zeolite composite product is described for use in environmental odor control applications, such as an alternative daily cover for landfills, a cover for compost piles, or compost bags. The zeolite composite product reduces odorous and/or toxic gas emissions produced, e.g., by processes which break down waste and compostable materials. Certain embodiments provide an ion exchanged zeolite paper product that offers a cost-effective biodegradable alternative for waste odor control applications.

One aspect provides a waste odor control composite including a fiber web and one or more zeolites containing between about 0.2% and about 4% Zn by weight, and between about 0.4% and about 4% by weight of one or more metals chosen from K, Li, Mg, Ba and Fe. In at least some embodiments, the odor control composite has a weight per unit area between about 30 g/m² and about 250 g/m² and a tensile strength between about 10 Nm/g and about 200 Nm/g.

Another aspect provides an odor control composite including a fiber web. One or more zeolites is incorporated within the fiber web, contains between about 0.2% and about 4% Zn by weight, and between about 0.4% and about 4% by weight of one or more metals chosen from K, Li, Mg, Ba and Fe, and has a median particle size of less than about 50 microns with 95% of the particles smaller than about 100 microns. Further, one or more zeolites is coated on a surface of the fiber web, contains between about 0.2% and about 4% zinc by weight, and between about 0.4% and about 4% by weight of one or more metal ions chosen from K, Li, Mg, Ba and Fe, and has a median particle size of less than about 25 microns with 95% of the particles smaller than about 50 microns.

In some embodiments of the above aspects, the odor control composite has a weight per unit area between about 40 g/m² and about 150 g/m². In some embodiments, the odor control composite further includes an additional natural or synthetic zeolite. In some embodiments, the fiber web comprises plant based cellulose fibers, for example, wood pulp. In certain embodiments, at least one zeolite contains between about 1% and about 3% Zn by weight. In certain embodiments, at least one zeolite contains between about 0.4% and about 4% by weight of one or more metals chosen from K, Li, Mg and Ba. In some embodiments, the composite is configured as an alternative daily cover for a landfill, for example, being configured as a roll having a width of at least about 36 inches and a diameter of at least about 24 inches. In some embodiments, the composite is configured as a composting bag.

Also provided is a method of controlling odor from a landfill by covering at least a portion of the landfill with an alternative daily cover comprising an odor control composite according to the above aspects. In some embodiments, the cover is ballasted, for example, by placing waste derived ballast, sand, boiler ash, or ground organic matter on the unrolled cover, or placing weights on a surface of the cover as it is unrolled.

Yet another aspect provides a method of making an odor control composite. The method includes contacting at least one zeolite with a solution of one or more metal ions, whereby the one or more metal ions diffuses into the zeolite to form at least one ion exchanged zeolite. Particles of at least one ion exchanged zeolite are prepared having a median particle size of less than about 50 microns with 95% of the particles smaller than about 100 microns. A fiber slurry is formed by contacting fibers with a liquid, and the zeolite particles are incorporated into the fiber slurry. A fiber web is formed from the slurry. Particles of at least one ion exchanged zeolite are prepared having a median particle size of less than about 25 microns with about 95% of the particles smaller than about 50 microns, and applied to one or more surfaces of the fiber web.

In some embodiments of the method, the fiber web is formed into an alternative daily cover for a landfill, for example, as a roll having a width of at least about 36 inches and a diameter of at least about 24 inches. In some embodiments, the fiber web is formed into a compost bag. In certain embodiments, the zeolite is contacted with a solution containing one or more metal ions chosen from $Zn^{+2}$, $K^+$, $Li^+$, $Mg^{2+}$, $Ba^{2+}$, $Fe^{2+}$ and $Fe^{3+}$. For example, in some instances clinoptilolite is contacted with a solution containing $Zn^{+2}$. In certain embodiments, a fiber slurry is formed by combining wood pulp with water. In some embodiments, the fiber web is formed by a wet-laid process, a fourdrinier or twin wire forming process.

BRIEF DESCRIPTION OF THE DRAWINGS

The following drawings are for the purpose of illustration only, and are not intended to be limiting.

FIGS. 2A-B are schematic drawings of the paper test chamber of a screening reactor used for testing ion exchanged zeolite paper samples for $H_2S$ absorption as described in Example 3 below.

DETAILED DESCRIPTION

Figure 1:
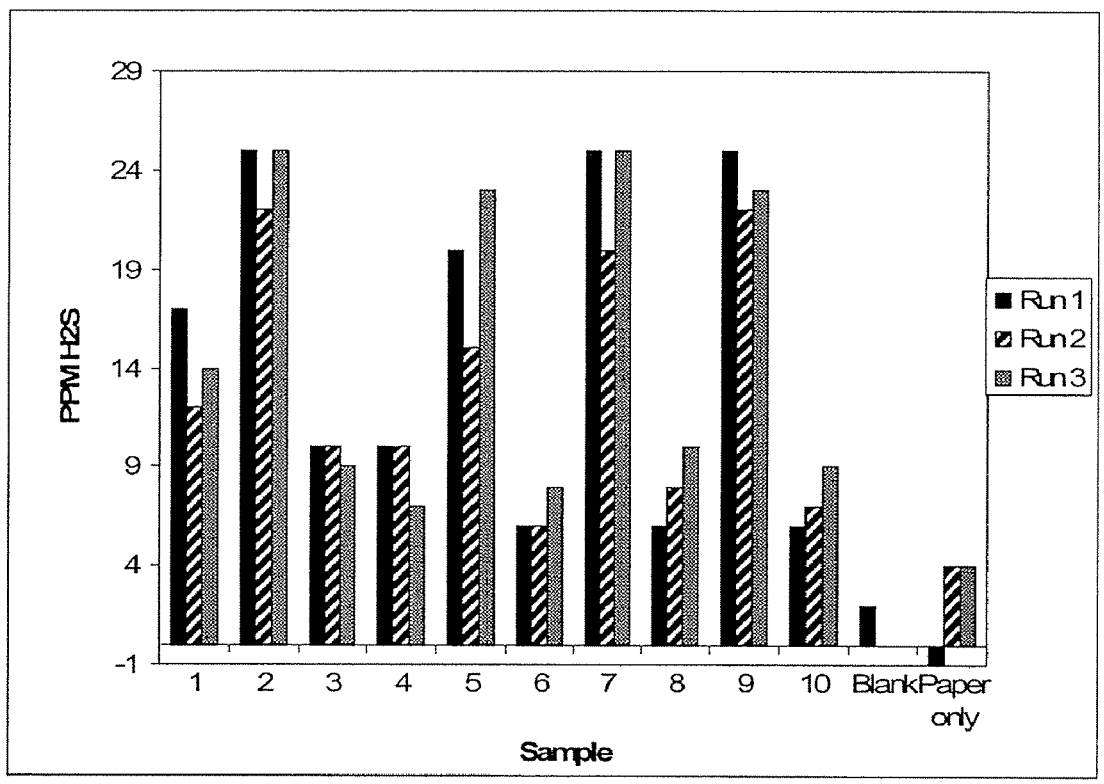
FIG. 1 is a plot showing the results (ppm $H_2S$ detected) for ion exchanged zeolite paper samples and control samples tested for $H_2S$ absorption as described in Example 1 below.

Odor control composite products as described herein have many "eco-friendly" uses in a variety of applications where waste is disposed and breaks down to produce odorous gas. Certain embodiments provide products useful in, for example, large scale odor reduction at municipal landfills and municipal compost sites, as well as consumer composting products such as biodegradable compost bags. According to certain embodiments, paper products are produced using wood pulp or other paper-making fibers mixed with a zeolite-based additive, some or all of which has been modified using an ion exchange process to promote efficacy in the absorption and remediation of odorous compounds. In some embodiments, an ion exchanged zeolite paper product is deployed as an alternative daily cover for a municipal solid waste landfill.

Odor Control Composite Material

Certain embodiments provide a biodegradable composite material with a composition designed for reducing odor. In at least some embodiments, the composite has a fiber web structure, for example, a paper product. In some embodiments, a composite material is prepared from a web of plant-based, synthetic or mineral fibers, with one or more zeolites dispersed throughout the web and/or applied to one or more surfaces of the web. In some embodiments, one or more dry strength agents, dyes, retention aids, defoamers, sizing agents, coating binders, and/or other additives used to produce paper and paperboard products are also included. Examples of suitable fibers include, without limitation, wood or other plant based cellulose fibers. In certain embodiments, wood pulp is used. In some embodiments, a fiber web article is produced with little or no alkaline buffer to promote physical strength loss and degradation of the fibrous web over time.

The fibers are formed into a web (e.g., a membrane or sheet), for example, using a wet-laid or dry-laid paper making technique. Such techniques are well-known to those skilled in the art, for example, as described in Smook, Gary A., *The Handbook for Pulp and Paper Technologists*, 3rd Ed., Tappi Press (2003), which is incorporated herein by reference. Examples of suitable processes include, without limitation, fourdrinier or twin wire forming processes.

By way of non-limiting example, in one embodiment a paper article is prepared containing up to about 2% by weight of the paper article of an ion exchanged zeolite, with the balance of the composition made up of wood pulp, e.g., bleached northern softwood kraft pulp. The ion exchanged zeolite is prepared using techniques as described in Breck, Donald W., *Zeolite Molecular Sieves: Structure, Chemistry* and Use, John Wiley and Sons (1974), which is incorporated herein by reference. A paper web is formed from the wood pulp using a traditional fourdrinier paper making process. A zeolite slurry is dispersed over both sides of the web using a puddle size press applicator. One suitable example of a particle size distribution for the zeolite is one with a median particle size between about 0.2 microns and about 50 microns, with at least 95% of the particles having a diameter of less than about 100 microns, as measured by a laser scattering particle size analyzer such as the Horiba LA-300 instrument. A final paper article having a basis weight of approximately 95 g/m² was produced by this method.

In certain embodiments, a fiber web article has a weight per unit area in the range of about 15 to 500 g/m², for example, between about 30 and about 250 g/m², between about 30 and about 200 g/m², or between about 40 and about 150 g/m². Basis weight is determined using Tappi Standard Test Method T410 om-02. In some embodiments, the tensile strength of a fiber web article ranges from about 10 Nm/g to about 200 Nm/g, for example, between about 20 Nm/g and about 150 Nm/g, as measured according to Tappi Standard Test Method T-494.

Zeolite Composition

In certain embodiments, one or more zeolites is incorporated into and/or applied to one or more surfaces of a fiber web as described above to provide odor absorbent properties. The term "zeolite" is used here in its generic sense and refers to crystalline inorganic molecular sieves such as aluminophosphates, silicon aluminum phosphates, microporous borosilicates, titanosilicates and titanoaluminosilicates, as well as microporous aluminosilicates and their silica analogs, having a framework structure consisting of nanopores and interconnected cavities which can be occupied by ions and/or water molecules, both of which have considerable freedom of movement permitting ion exchange and reversible dehydration. In contrast to amorphous materials these crystalline structures contain regular arrays of intracrystalline pores (nanopores) and voids of uniform dimensions. A typical naturally occurring zeolite is the mineral clinoptilolite with formula $(Ca,Na,K)_{2-3}Al_3(Al,Si)_2Si_{13}O_{36} \cdot 12(H_2O)$. As used herein, "ion exchanged zeolite" refers to a natural or synthetic zeolite that has been modified by an ion exchange process to increase the content of one or more metal ions in the zeolite.

For example, in some embodiments one or more ion exchanged zeolites is incorporated into a biodegradable composite for use, e.g., as a paper delivery system capable of reducing hydrogen sulfide emissions at municipal landfills when used as an alternative daily cover. In certain embodiments, a combination of one or more ion exchanged zeolites and one or more unexchanged natural zeolites is employed, which can further enhance the odor absorbing capabilities of the product. "Absorption" is used herein in its general sense, to include also adsorption and chemical reaction or any other way in which odiferous molecules may be trapped. Unexchanged zeolites, e.g., clinoptilolite, can absorb ammonia compounds and volatile organic compounds (VOC's), which are problematic for both landfills and composting operations. Suitable zeolites for use in the compositions described herein include, without limitation, naturally occurring or synthetic zeolites such as clinoptilolite, mordenite, erionite, chabazite, phillipsite, heulandite, analcime and combinations thereof. In certain embodiments, naturally occurring zeolites are used. Any of the natural or synthetic zeolites can be used, alone or in combination, in ion exchanged or unexchanged form or both. In certain embodiments, at least one ion exchanged clinoptilolite is employed.

In certain embodiments one or more zeolites included in the odor control composite has been modified through an ion exchange or impregnation process to contain up to about 5% by weight total of one or more metal ions such as, for example, $Zn^{+2}$, $Fe^{+2}$, $Fe^{+3}$, $Mn^{+2}$, $Mg^{+2}$, $Ca^{+2}$, $Ba^{+2}$, $Li^+$ or $K^+$. In some embodiments, the zeolite is modified to contain between about 1% and about 5% by weight, for example, between about 2% and about 5%, or between about 3% and about 5% by weight, of the one or more metal ions. In certain embodiments, the content of one or more multivalent metal ions is increased to facilitate binding of reduced sulfur compounds. Suitable multivalent metal ions include without limitation $Zn^{+2}$, $Fe^{+2}$, $Fe^{+3}$, $Mn^{+2}$, $Mg^{+2}$, $Ca^{+2}$ and combinations thereof. By way of non-limiting example, in certain embodiments, a zeolite, e.g., clinoptilolite, is modified to contain about 0.5% Mg and about 3% Zn, about 4% K and about 1% Zn, about 0.2% Li and about 2% Zn, or about 4% Ba and about 1% Zn. In some embodiments, an ion exchanged zeolite is prepared to contain between about 1% and about 5% Zn, for example, between about 1% and about 3% Zn. Ion exchanged zeolites can be prepared using techniques as described in Breck, Donald W., Zeolite Molecular Sieves: Structure, Chemistry and Use, John Wiley and Sons (1974), which is incorporated herein by reference. One example of a suitable ion exchange process is described in Example 1 below.

The particle size of one or more zeolites included in a biodegradable odor control composite can impact the manufacture, quality and performance of the product. In certain embodiments of a biodegradable composite described herein, the particle size of one or more zeolites is selected to promote ease of manufacture and/or odor absorbent performance. The particle size of the zeolite can be controlled by appropriate levels of grinding and sieving.

Smaller particle size of a zeolite generally has been found to promote odor reducing properties as well as metal ion exchange (e.g., zinc) for the zeolite, due to the increased surface area of the smaller particles. The increased surface area typically improves the adsorption of odorous gas molecules, and reduces the distance between the average metal ion site in the zeolite and the surface of the zeolite particle. This promotes improved hydrogen sulfide conversion, and reduced diffusion time.

However, the particle size of a zeolite also influences its incorporation into a fiber web, and the quality of the resultant web. The particle size affects the ease of retaining the particles in the fiber structure as the web is formed. In general, the percentage of particles retained in the forming web increases as the particle size increases. Retention of small particle sizes can be improved by the use of charged polymers, but this can increase the cost of the product. Also the cost of reducing the size of the particles tends to increase as the size of the particles is reduced. Particles with median particle sizes of less than about 50 microns and at least 95% of the particles less than about 100 microns (as measured by a laser scattering particle size analyzer such as the Horiba LA-300 instrument) are typically used in filling applications to promote strength and smoothness of the web. Zeolites can also be coated onto one or more surfaces of the web. Generally, zeolites with smaller particle sizes are used for coating applications, such as particles with a median size less than about 25 microns and at least 95% of the particles less than about 50 microns, to promote uniformity of the coating application.

In some instances, a zeolite composition is employed containing one or more zeolites each with a median (based on volume of particles) particle size between about 0.05 microns and about 50 microns with at least 95% of the particles less than about 100 microns, as measured using a laser scattering particle size analyzer, such as the Horiba LA-300.

In some embodiments, one or more zeolites is incorporated into a fiber web structure, e.g., as part of the initial fiber slurry. In some embodiments, one or more zeolites is coated onto one or both sides of the web. One or more binders, rheology modifiers, defoamers and/or other coating additives optionally can be included in the coating formulation. In certain embodiments, one or more zeolites are both incorporated into the fiber web and also coated onto one or both surfaces of the structure. For example, in some instances one or more larger particle size zeolites are incorporated into the fiber web, while one or more smaller particle size zeolites are coated onto one or more surfaces of the web. Non-limiting examples of suitable particle size distributions for filling and coating applications are as described above.

Alternative Daily Cover and Composting Applications

In some embodiments, an odor reducing composite product as described herein is used in large scale applications, for example, being deployed as an alternative daily cover membrane for a municipal solid waste landfill. Such a cover can be used to cover areas, for example, as large as about 9,500 square feet, which represents a typical landfill's working face. The biodegradable cover with low fill capacity can be deployed and left in place, becoming part of the fill. An alternative daily cover as described herein provides an effective means of odor reduction not provided by other alternative daily covers, and may also afford reduced cost and manpower requirements for deployment.

In certain embodiments, a fiber web article containing and/or coated with one or more zeolites as described herein is provided in rolls, for example, having a width of at least about 36 inches and a diameter of at least about 24 inches. The article is deployed as an alternative daily cover by unrolling the web over the exposed surface of a landfill, or compost pile. The unrolled web thus provides a biodegradable tarp that can be left in place without removal. The weight of the roll firmly sets the article in place. Suitable methods to ballast the article include, without limitation, using a sufficient amount of ballast, such as waste derived ballast, sand, boiler ash, or ground organic matter to prevent blowing or disturbance of the cover from wind; or placing weights (e.g., chains, cables, or weighted rope) on the surface of the web as it is unrolled, which can then be retrieved for re-use. Such a deployment method typically does not place high stress levels on the article, and allows for effective use of relatively low weight and low cost product designs. Thus, a web according to certain embodiments herein provides a relatively thin, light weight, low strength alternative daily cover. In some embodiments, the web has a tensile strength of about 70 Nm/g. Webs having increased tensile strength can be prepared; however, high tensile strength is not typically required for a nonreusable ADC that is deployed and left in place.

Paraskaki et al., *Waste Management and Research* 23:199-208 (2005), published a study of the gaseous emissions from a municipal solid waste landfill, focusing on a 870,000 m$^2$ waste site in Greece that was closed in the year 2000. The highest concentrations of $H_2S$ observed at this site were 3.6 mg/m$^3$, which corresponds to approximately $6.3 \times 10^{16}$ molecules/liter. It is estimated that one pound of an alternative daily cover according to certain embodiments herein could remediate (remove $H_2S$ from) approximately 1000 L of air from above the landfill studied by Paraskaki et al., based on the highest observed concentrations of $H_2S$.

In some embodiments, a fiber web article containing and/or coated with one or more zeolites as described herein is used to manufacture compostable bags or compost pile covers. The use of zeolite paper articles for compostable bags combines the odor absorption capability with an organic waste container which is compostable under controlled aerobic conditions into its component compounds. According to certain embodiments, a zeolite paper article for composting applications is made using processes as described above and for the alternative daily cover. As a non-limiting example, in some embodiments, the paper is an unbleached Kraft with zeolite applied as a coating or in the base paper, and the paper is applied as a cover for compost piles. In some embodiments, the paper is formed into a one- or multi-ply bag in which one or more of the paper layers contains a zeolite. Bags can be formed, for example, at 3 gallon up to 60 gallon sizes. As described above, the zeolite used in the paper for the bags or compost pile covers can include one or more natural or synthetic unmodified zeolites, one or more zeolites modified to incorporate metal ions, or a combination thereof. In certain embodiments, the zeolite composition helps to control a variety of potential odors from decomposing organic waste, including volatile organic compounds, ammonia, and sulfur containing compounds.

The following non-limiting examples further illustrate certain embodiments.

EXAMPLE 1

Ion Exchanged Zeolite

A set of ion exchanged zeolite samples was produced and used to evaluate factors (exchanged ion, zeolite type) that could contribute to the ability of the material to adsorb hydrogen sulfide. Three different zeolites were chosen: faujasite (FAU), clinoptilolite (CLIN) and ZSM-5 (MFI). The zeolite samples prepared, as well as the cation exchange capacity (CEC) for the three types of zeolite, are summarized in Table I.

TABLE I

Ion Exchanged Zeolite Samples

| Sample | Cation | Zeolite | *Ion Size and Charge |
|---|---|---|---|
| 1 | Li | FAU | S1 |
| 2 | Mg | CLIN | S2 |
| 3 | K | FAU | L1 |
| 4 | Ba | MFI | L2 |
| 5 | Na | CLIN | M1 |
| 6 | Ca | MFI | M2 |
| 7 | Ba | CLIN | L2 |
| 8 | Li | MFI | S1 |
| 9 | None | CLIN | 0 |
| 10 | None | FAU | 0 |

| | Cation Exchange Capacity (meq/g) |
|---|---|
| MFI | 1.22 |
| FAU | 4.88 |
| CLIN | 0.8-1.2 |

*S, M, L: small, medium, large ionic radius, 1 and 2 are +1 and +2 ionic charge

Several grams of each ion exchanged zeolite were prepared. The following ion exchange procedure was used, which is described for clinoptilolite but applies similarly to the other zeolites, whose cation exchange capacities are identified in Table I. The exchange capacity of the clinoptilolite zeolite was assumed to be 1.0 meq/g. Exchange conditions were set to be 10:1, and 2.0 g of clinoptilolite were exchanged for each ion.

Example: $BaCl_2$: 208.25 g/mol, therefore 0.1041 g of $Ba^{2+}$ ions in solution For a 10:1 exchange solution, (1.041 g $BaCl_2$/1.0 g zeolite)*2.0 g zeolite=2.082 g $BaCl_2$ Roughly 1 g of each zeolite sample was incorporated into a paper handsheet. Handsheets were prepared according to Tappi Standard Method T-205 and mixing the zeolite into the fiber slurry prior to forming the handsheet. A retention aid (cationic polyacrylamide, Ciba Specialties Percol 175) was also added at a dosage rate of 0.5 kg/ton of fiber to the sheet mold during the formation process to aid in the retention of the fine particles.

The handsheets were subsequently tested for absorption of hydrogen sulfide by placing samples of each handsheet in an airtight Tedlar bag that was subsequently filled with 25 ppm hydrogen sulfide gas balanced with nitrogen. The bags were allowed to sit for 24 hours, at which time they were pumped out through a hydrogen sulfide detector (RAE Systems), an electrochemical sensor with a detection limit of 1 ppm for hydrogen sulfide. The amount of hydrogen sulfide detected for each bag was subtracted from 25 ppm in order to compare the relative ability to absorb hydrogen sulfide between the different paper samples.

FIG. 1 shows the results of three different tests of each of the 10 handsheet samples as well as an empty bag (blank) and samples of paper which did not contain zeolite (paper only). The "blank" and the "paper only" samples showed very little absorption. Samples 2, 5, 7, and 9, which each contained ion exchanged clinoptilolite, showed the highest levels of absorption in these experiments.

EXAMPLE 2

Ion Exchanged Clinoptilolite Compositions

Based on the results of Example 1, a second set of samples was prepared based on clinoptilolite in which the ion size, ion type, and zeolite mesh size were varied. Different metal salts were used in ion exchange reactions with the natural clinoptilolite. Single metal salt and dual metal compositions were studied.

Table II details compositions prepared in these experiments.

TABLE II

Ion Exchanged Clinoptilolite Samples

| Sample # | Ion | % Zinc | Mesh Size* | Ion Size (Angstroms) | Charge |
|---|---|---|---|---|---|
| 1 | Mg | High | 325 | 0.66 | 2 |
| 2 | Ba | High | 325 | 1.36 | 2 |
| 3 | Ba | Low | 200 | 1.36 | 2 |
| 4 | K | High | 325 | 1.33 | 1 |
| 5 | K | Low | 200 | 1.33 | 1 |
| 6 | Li | High | 200 | 0.68 | 1 |
| 7 | Li | Low | 325 | 0.68 | 1 |
| 8 | Mg | Low | 325 | 0.66 | 2 |
| 9 | K | High | 200 | 1.33 | 1 |
| 10 | Mg | Low | 200 | 0.66 | 2 |
| 11 | Ba | Low | 325 | 1.36 | 2 |
| 12 | Li | High | 325 | 0.68 | 1 |
| 13 | Ba | High | 200 | 1.36 | 2 |
| 14 | None | None | 200 | 0 | 0 |

*Mesh Size 325 = median 9.2 microns; 95% less than 28 microns Mesh Size 200 = median 8.1 microns; 95% less than 23 microns as measured by Horiba LA-300 laser scattering particle size analyzer In some experiments an additional ion (zinc) was tested to determine the effect of using a "reactive" ion, i.e., one which could potentially form a metal sulfide material when exposed to hydrogen sulfide. The % zinc (Zn) was modified by either not exchanging with Zn (Low) or by exchanging in 80/20 zinc to co-exchanged ion solution (High). The samples were all prepared using the same exchange conditions, and then the resultant exchanged material was characterized using Inductively Coupled Plasma-Atomic Emission Spectroscopy (ICP-AES). Ion exchange was carried out as described for Example 1. For samples requiring the presence of 2 types of cations (zinc and another cation), exchange of both cations was conducted simultaneously.

The results of the ICP-AES test are summarized in Table III and show the atomic composition of the zeolite samples 1-14, which were prepared as shown in Table II, and were later used for the screening test paper handsheets as described in Example 3 below. The samples were prepared for ICP-AES by microwave digestion in aqua regia (3 HCl:1 $HNO_3$), and then diluted to a final volume (100 mL) for analysis. This preparatory method yields accurate results for all the atomic species in the zeolite with the exception of the silicon. However, the exchanged materials were well characterized by looking at aluminum and the various exchanged ions (K, Mg, Ba, Li, and Zn). Table III lists the detected concentrations of each atomic species by either weight percent, or in the case of trace elements, the micrograms detected versus gram of sample.

TABLE III

ICP-AES Results for Ion Exchanged Clinoptilolite Samples

| Sample | Mass (g) | Al % | Fe % | K % | Mg % | Si % | Ba ug/g | Li ug/g | Na ug/g | Zn ug/g |
|---|---|---|---|---|---|---|---|---|---|---|
| 1 | 0.1025 | 3.95 | 1.63 | 2.41 | 0.42 | 1.92 | 733 | 21 | 616 | 28293 2.83% |
| 2 | 0.0993 | 4.16 | 1.69 | 1.70 | 0.28 | 3.52 | 37915 3.79% | 22 | 143 | 11229 1.12% |
| 3 | 0.1042 | 4.19 | 1.68 | 1.56 | 0.28 | 6.79 | 47457 4.74% | 23 | 91 | 12.0 |
| 4 | 0.1048 | 4.17 | 1.67 | 4.18 | 0.27 | 3.51 | 326 | 21 | 87 | 11784 1.18% |
| 5 | 0.0969 | 4.26 | 1.66 | 4.87 | 0.27 | 0.40 | 127 | 22 | 50 | 6.2 |
| 6 | 0.1041 | 4.22 | 1.90 | 2.38 | 0.30 | 2.30 | 753 | 251 | 535 | 20653 2.06% |
| 7 | 0.0994 | 4.24 | 1.14 | 2.49 | 0.24 | 5.45 | 844 | 3355 0.34% | 517 | 0.0 |
| 8 | 0.1011 | 4.37 | 1.86 | 2.64 | 0.57 | 4.25 | 801 | 30 | 1147 | 10.4 |

TABLE III-continued

ICP-AES Results for Ion Exchanged Clinoptilolite Samples

| Sample | Mass (g) | Al % | Fe % | K % | Mg % | Si % | Ba ug/g | Li ug/g | Na ug/g | Zn ug/g |
|---|---|---|---|---|---|---|---|---|---|---|
| 9 | 0.1028 | 4.42 | 1.91 | 4.56 | 0.29 | 3.96 | 340 | 25 | 96 | 14105 1.41% |
| 10 | 0.1032 | 4.31 | 1.52 | 2.54 | 0.53 | 5.32 | 823 | 19 | 1250 | 3.4 |
| 11 | 0.1058 | 4.26 | 1.71 | 1.57 | 0.29 | 4.74 | 48015 4.80% | 26 | 69 | 8.0 |
| 12 | 0.1016 | 4.24 | 1.72 | 2.33 | 0.28 | 3.44 | 782 | 259 | 532 | 18553 1.86% |
| 13 | 0.0973 | 4.13 | 1.72 | 1.72 | 0.28 | 3.82 | 39157 3.92% | 23 | 143 | 11048 1.10% |
| 14 | 0.104 | 4.41 | 1.76 | 2.70 | 0.32 | 8.48 | 818 | 24 | 2279 | 47 |

The ICP-AES results show that the sample compositions correlate with the design of high/low zinc, as well as high levels of the designated co-exchanged ions. As shown in Table III, the following ion levels were increased according to the design of the exchange conditions: Mg and Zn in sample 1, Ba and Zn in sample 2, Ba in sample 3, K and Zn in sample 4, K in sample 5, Li and Zn in sample 6, Li in sample 7, Mg in sample 8, K and Zn in sample 9, Mg in sample 10, Ba in sample 11, Li and Zn in sample 12, Ba and Zn in sample 13. Bold typeface and increased font sizes are used in Table III to highlight these ion levels.

EXAMPLE 3

Paper Handsheet Screening Study

The ion exchanged clinoptilolite samples prepared according to Example 2 were incorporated into paper handsheets prepared as described in Example 1. The paper handsheets including zeolite samples 1-14 were tested using a screening reactor. In the reactor, $H_2S$ gas had to pass through the paper samples in order to reach a detector.

The paper test chamber of the screening reactor is shown in FIG. 2. FIG. 2A shows the paper test reaction chamber ready for a paper sample. A paper sample 200 is loaded onto the surface 202. FIG. 2B shows the paper test reaction chamber closed and ready to perform a test. The paper test chamber of the screening reactor was modular, and equipped with "dry break" quick disconnect fittings 204 to facilitate the ease of sample loading. The diameter of the test chamber was 1.5 inches.

The gas delivery system to the screening reactor was designed to mix two different gases proportionally and to operate with an automated controller to ensure that the gas mixture was delivered to the reaction chamber in a repeatable fashion. For this experiment the gases used were hydrogen sulfide and nitrogen. A standard reference gas cylinder (BW Technologies, Calgary, Canada) with a concentration of 25 ppm was used as the source of $H_2S$. Automated control of the gas input was controlled by the SmartRelay® (IDEC). For this study, the SmartRelay® used internal programming to control two solenoid actuated valves which input small amounts of gas into the reaction system at a prescribed time interval. The gas input pressure to each of the solenoid valves was maintained by micro pressure regulators mounted upstream of the valves. This pressure regulation insured that the same amount of gas was introduced into the reactor each time the valve was actuated.

Figure 3:
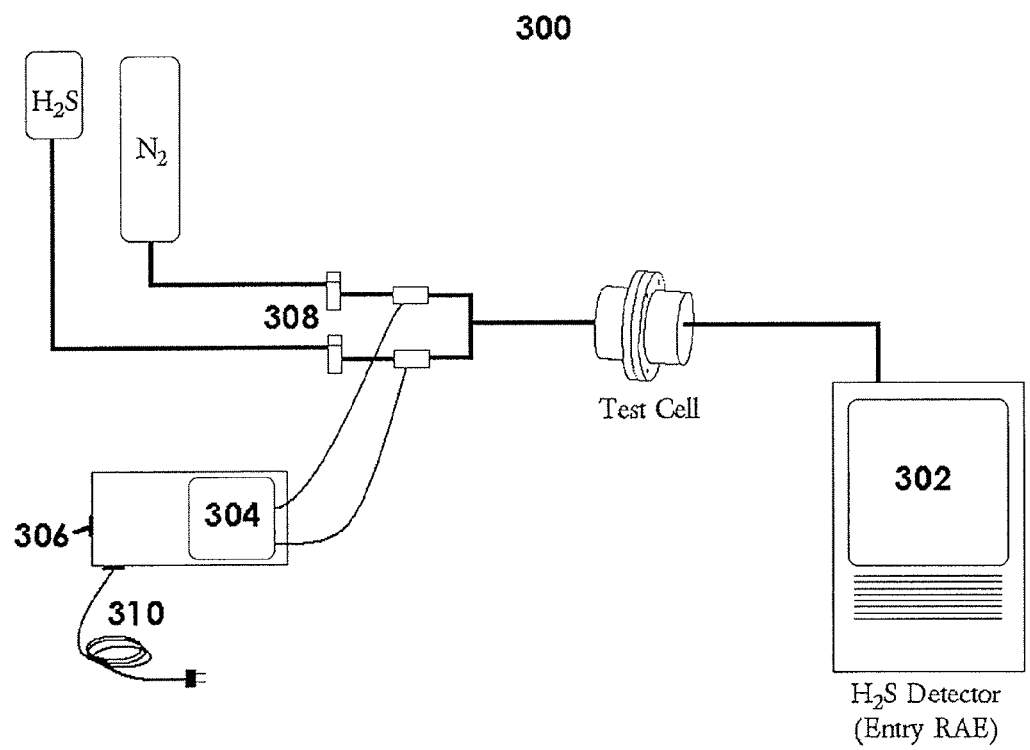
FIG. 3 is a schematic drawing of the automated fluid delivery system for the screening reactor used for testing ion exchanged zeolite paper samples for $H_2S$ absorption as described in Example 3.

The automated fluid delivery system is shown in FIG. 3. The illustrated system 300 includes an $H_2S$ detector 302 (RAE Systems), an automated gas input controller 304, a main power switch 306, upstream regulators 308, and 24 VDC input 310. The RAE detector 302 with an electrochemical $H_2S$ sensor was capable of detecting $H_2S$ down to 1 ppm levels.

The paper handsheets made with the clinoptilolite samples 1-14 prepared according to Example 2 were tested in the screening reactor. $N_2$ used to purge the system between experiments was set to 5 psi and the $H_2S$ tank was set to 500 cc/min. The system was purged on startup to remove any air and residual $H_2S$. Each test was started by loading a 1.5 inch diameter paper sample into the test chamber. The system was purged with $N_2$ and then allowed to run until 10 ppm of $H_2S$ was detected. The total elapsed time of the experiment and the pulses of $H_2S$ injected into the system were displayed on the SmartRelay. The ppm $H_2S$ detected through the paper sample was measured by the RAE detector using a calibrated electrochemical sensor.

Data for the paper test samples was recorded on video which captured both the shot number (number of hydrogen sulfide gas "pulses") and the RAE detector display (ppm hydrogen sulfide detected). Data was then recorded into a worksheet and plotted to show detected hydrogen sulfide levels versus time (number of "shots").

Figure 4:
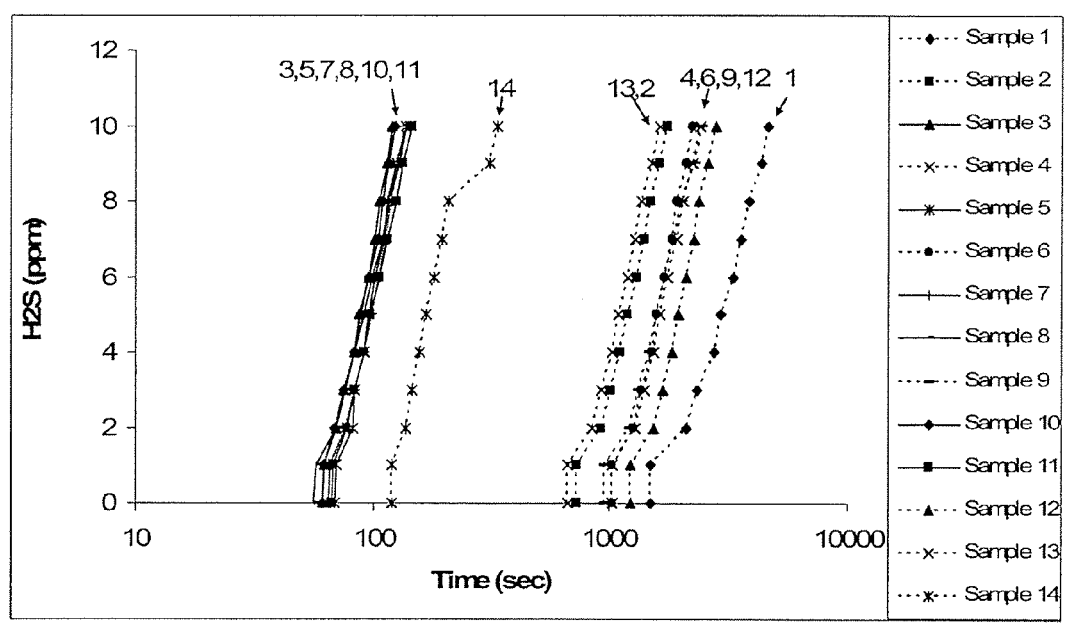
FIG. 4 is a plot of "breakthrough" times (ppm $H_2S$ v. time) for ion exchanged zeolite paper samples that were tested for hydrogen sulfide absorption as described in Example 3.

FIG. 4 shows the plots of "breakthrough" times for the 14 different samples screened. The breakthrough time, representing the appearance of $H_2S$ at the lowest detectable limits, is directly proportional to the sample's adsorptive capacity for hydrogen sulfide. The samples clustered into two distinct groups: one group with breakthrough prior to 100 seconds (samples 3, 5, 7, 8, 10 and 11), and another with breakthrough around 1000 seconds (samples 1, 2, 4, 6, 9, 12 and 13). The results revealed enhanced hydrogen sulfide absorption for the samples which included zinc.

Figure 5:
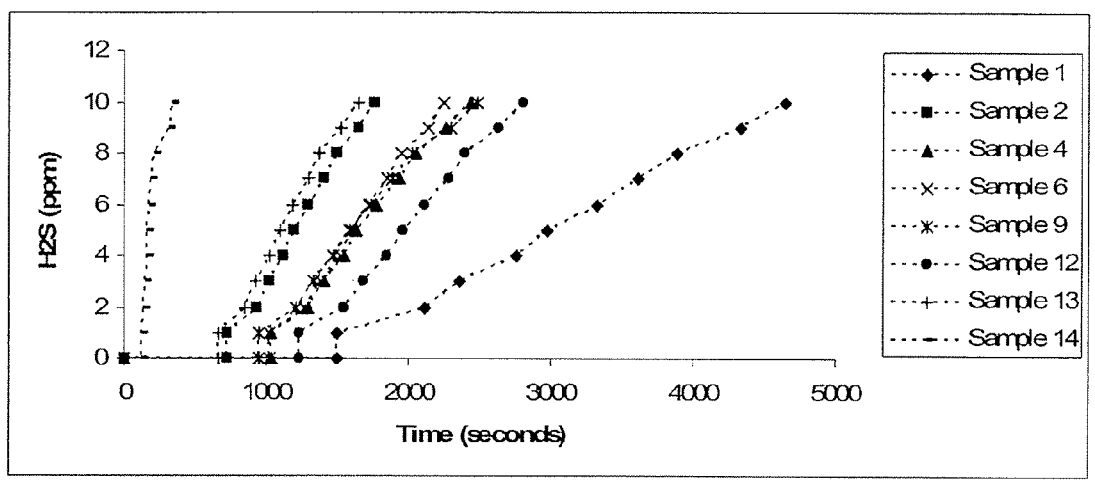
FIG. 5 is a plot of ppm $H_2S$ versus time for ion exchanged zeolite paper samples including zinc and a control sample that were tested for hydrogen sulfide absorption as described in Example 3.

FIG. 5 is a plot of $H_2S$ detected versus time for six different formulations that included zinc (samples 1, 2, 4, 6, 9, 12 and 13) along with the unexchanged clinoptilolite (control) sample (sample 14). The unexchanged clinoptilolite control sample (sample 14) had the steepest slope, indicating the most rapid rise in $H_2S$, and the earliest first appearance of $H_2S$. Sample 1 showed the best performance in this experiment, as demonstrated by the slowest rise time and the latest breakthrough time for $H_2S$.

Figure 6:
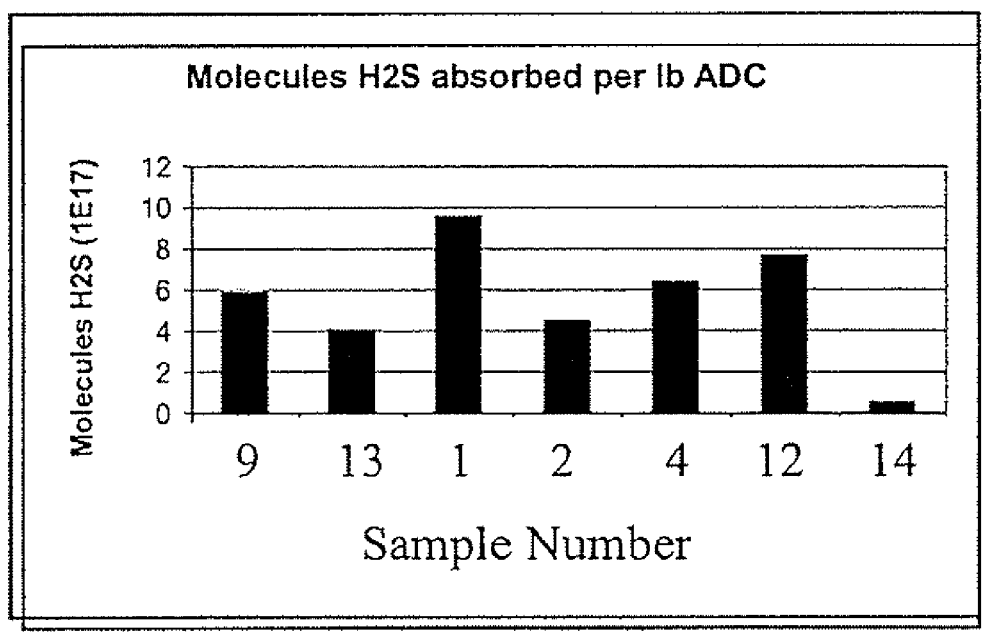
FIG. 6 is a plot of adsorption capacities for ion exchanged zeolite paper samples (molecules $H_2S$ absorbed per pound of paper alternative daily cover) that were tested for hydrogen sulfide absorption as described in Example 3.

Information regarding total $H_2S$ adsorption capacity can be calculated from these results. This was done using the concentration of the test gas (25 ppm $H_2S$), the total volume of gas passed through the paper sample, and the mass of the paper sample. The total volume of $H_2S$ exposed to the paper sample until the detector began sensing the presence of gas was recorded as the breakthrough volume. Adsorption capacities of the samples are shown in FIG. 6.

EXAMPLE 4

Leachate Testing

Environmental conditions can impact the performance of an alternative daily cover on a landfill. Tests were performed to examine the effect of water and pH on a zeolite with enriched metal ion content and on a paper sample containing a zeolite with enriched metal ion content. These samples were prepared using the methods described in Examples 1-3.

Dried silver (I) exchanged faujasite was suspended in buffered solutions with pH values of 6.0, 7.0, and 8.0. After stirring for 1 hour the samples were centrifuged, supernatants decanted and then filtered using a 0.2 micron filter. The resulting supernatants were analyzed for silver content using ICP-AES. The concentration of silver in the leachate was determined to be 0.7 ppm, 0.8 ppm, and 0.6 ppm for pH values of 6.0, 7.0, and 8.0 respectively.

A 3.5 cm diameter circle taken from a paper handsheet prepared as described in Example 1 using a zeolite having the composition of Sample 1 in Table III was exposed to allyl sulfide and then tested for composition stability by suspending it in water for 1 hour under constant vigorous stirring. The sample was centrifuged and the supernatant was tested for the presence of the ion exchanged zeolite by ICP-AES. Less than 3% of the zeolite was found in the supernatant.

A 3.5 cm diameter circle taken from a paper handsheet prepared as described in Example 1 using a zeolite having the composition of Sample 1 in Table III was exposed to hydrogen sulfide and placed in a Tedlar bag with 20 mL of distilled-deionized water. After incubation for an hour the airspace in the bag was tested for release of $H_2S$, and none was found.

These leachate tests showed that little or no ion exchanged zeolite was removed from the paper sample, indicating that water did not reduce the odor absorbing efficacy of the paper.

EXAMPLE 5

Paper Roll Production

Based on the results of Examples 2-3, a roll of paper was produced. 2 pound batches of clinoptilolite were ion exchanged and then milled down to an appropriate size (median size 8 microns with 95% less than 344 microns measured on the Horiba LA-300) to be incorporated into the paper web using a size press. The exchange conditions were based on the lab scale amounts as described in Examples 1-2.

Again ICP-AES was used to test the batches of exchanged zeolite in order to confirm the actual composition. The results are summarized in Table IV.

TABLE IV

ICP-AES Results for Paper Roll Zeolite Batches

| Sample | Mass (g) | Al % | Si % | Mg % | Zn % |
|---|---|---|---|---|---|
| Original Sample 1 | 0.1025 | 3.95 | 1.92 | 0.42 | 2.8 |
| Batch 1 | | 2.92 | 0.26 | 0.58 | 0.1 |
| Batch 2 | | 3.08 | 0.18 | 0.53 | 0.23 |
| Batch 3 | | 3.46 | 5.47 | 0.59 | 0.29 |
| Batch 4 | | 3.44 | 5.05 | 0.59 | 0.32 |

These four batches were each significantly lower in % zinc as compared with the handsheet made from sample 1 of Example 2. This result was attributed to the lower salt concentrations used for the larger scale exchanges, as well as slow kinetics of exchange.

A fourdrinier former was used to produce a web made from northern softwood kraft with a basis weight of approximately 90 g/m². The web was then passed through a flooded nip size press where an aqueous slurry of zeolite was applied to both sides of the sheet simultaneously and then the paper was dried to a moisture content of approximately 4% by weight of the paper. The concentration of zeolite in the slurry was adjusted to control the zeolite loading to between 1-5% of the weight of the paper. Each of the four batches was used in the paper production, but they were added separately so as to have sections of the paper which contained each of the unique zeolite formulations. As the paper was made, the sections of the roll were marked off.

EXAMPLE 6

Field Test of Zeolite Paper Tarps

Tarps made from the paper roll including zeolite Batch 4 as prepared in Example 5 were field tested for performance as a landfill cover. Data were collected to evaluate the performance of the tarp deployed in a landfill in the areas of durability, weathering and odor control (specifically the sequestration of $H_2S$).

Equipment and Materials Used at the Test Site:
Ac'scent® Emission Isolation Flux Hood (St. Croix Sensory, Lake Elmo, Minn.)
Vac'Scent® Vacuum Chamber (St. Croix Sensory, Lake Elmo, Minn.)
Grade 4.8 (99.998%) $N_2$ sweep gas and regulator (Advantage Gases and Tools)
Tedlar Bags, 1 and 5 Liter, (CELScientific)
Jerome 631-X $H_2S$ Analyzer (Arizona Instruments)
EntryRAE gas detector (RAE Systems)
Thermometer with humidity readout
Multimeter with thermocouple
4'×4' Tarps of the following formulations:
 1 Base Paper
 6 Tarp Formulation #4 (prepared according to Example 5, using zeolite Batch 4)
Weathering:

Two tarps were deployed for durability observations, and performed well throughout a four day test. During the test, the tarps were exposed to rain on days one and three, with rainfall totals of 0.13 inches and 0.02 inches, respectively. The tarps also encountered an average wind speed of 5 mph, with a high of 13 mph and a low of 0 mph, based on NOAA weather data. The tarps showed no visible signs of significant damage or degradation during the test.

$H_2S$ Ground Emission Variability:

Ground emission of $H_2S$ from the landfill was site and weather dependent, varying greatly based on atmospheric pressure and location. Even in increments as small as four feet across the working face of the landfill, large changes in $H_2S$ emissions were observed. To overcome this variability, tests were conducted concurrently for both above tarp and ground emissions at the same site.

Tarp Performance Test:

The engineered tarp showed promising performance in the area of $H_2S$ remediation. The engineered tarp, designated as tarp formulation #4, was deployed alongside a tarp constructed of only the base paper for a comparative study. The $H_2S$ emission for each test site was initially measured. The tarps were then deployed over the test sites and measurements were then taken immediately. Measurements comparing the ground emission with the above tarp readings were then taken at designated intervals to investigate how the tarps performed over time. The exposure time for each tarp was four hours.

Figure 7:
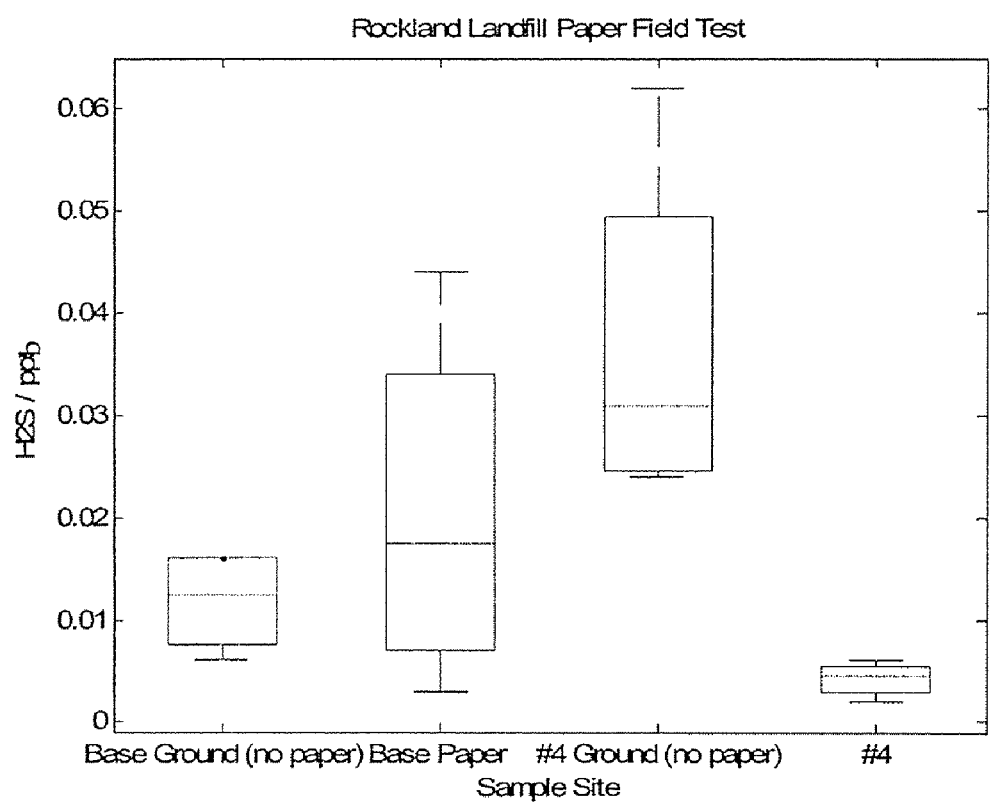
FIG. 7 is a modified box and whisker plot showing the performance (based on ppb $H_2S$ detected) of an ion exchanged zeolite paper tarp compared to a control base paper tarp deployed in a landfill as described in Example 6.

FIG. 7 shows the results of the $H_2S$ remediation performance testing. A modified box and whisker plot was used to statistically present the data due to the variability of $H_2S$ ground emissions over time. The average value of measured emissions is denoted by the line inside of the box. The box surrounding the average represents the variance in the data, in other words, where the data points cluster in relation to the average value. The variance shows how closely the data clusters around the average. The bars above and below the variance box represent the range of the data collected, where the bar above the box represents the highest value recorded and likewise, the bar below is the lowest.

The data in FIG. 7 show high variability in the base paper data, which is similar to the data collected from the ground only, suggesting that the base paper exhibited little control in the remediation of $H_2S$. The data for site "#4 ground" as compared to the "#4" tarp showed excellent results. As shown in FIG. 7, the $H_2S$ measurement levels recorded above the tarp over a four hour period were tightly clustered around the average, indicating that the #4 tarp was remediating the majority of $H_2S$ emitted from the ground beneath, even with large variations in ground emissions of $H_2S$ over the test period. If the #4 tarp were merely blocking the $H_2S$ emission, the variance in the data would have grown to indicate paper saturation similar to the results seen in the base paper.

Figure 8:
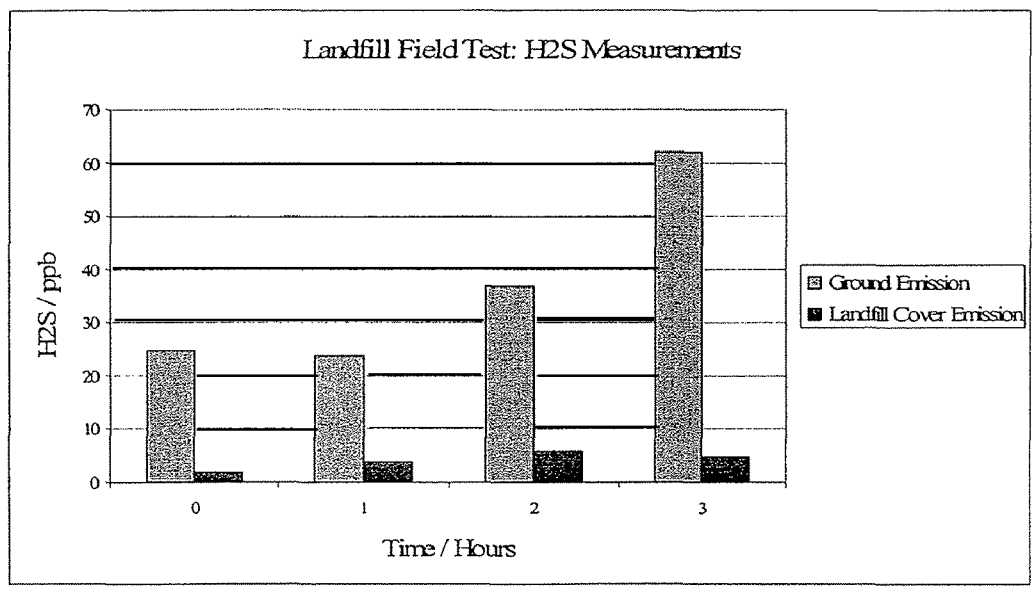
FIG. 8 is a plot of ppb $H_2S$ versus time comparing ground emission to emission through an ion exchanged zeolite paper tarp deployed in a landfill as described in Example 6.

FIG. 8 displays the data reported in FIG. 7 in a different way. In FIG. 8 the data for the ground emission is compared to the data for emission through tarp #4 over the three hour period for which data was collected. The data collection method attempted to control for the observed ground emission variation by sampling the same exact location "uncovered" and then placing the tarp over the ground and sampling through the tarp to acquire the "landfill cover emission" data.

In summary, the results shows that the tarp #4 formulation had the ability to control $H_2S$ emission better than the base paper with no zeolite additive. The wide variance of the base paper data more closely resembles the variance observed in the site measurements of the open ground, indicating that $H_2S$ was saturating and then passing through the base paper tarp in an uncontrolled fashion.

As will be apparent to one of ordinary skill in the art from a reading of this disclosure, the present invention can be embodied in forms other than those specifically disclosed above. The particular embodiments described above are, therefore, to be considered as illustrative and not restrictive. The scope of the invention is as set forth in the appended claims, rather than being limited to the examples contained in the foregoing description.

What is claimed is:

1. A waste odor control composite comprising:
   (a) a fiber web; and
   (b) one or more zeolites containing between about 0.2% and about 4% Zn by weight, and between about 0.4% and about 4% by weight of one or more metals chosen from K, Li, Mg, Ba and Fe,
   wherein the odor control composite has a weight per unit area between about 30 g/m² and about 250 g/m² and a tensile strength between about 10 Nm/g and about 200 Nm/g; and
   wherein the composite is configured as a composting bag.

2. An odor control composite comprising:
   (a) a fiber web; and
   (b) one or more first zeolites incorporated within the fiber web, wherein the one or more first zeolites contains between about 0.2% and about 4% Zn by weight, and between about 0.4% and about 4% by weight of one or more metals chosen from K, Li, Mg, Ba and Fe, and wherein the one or more first zeolites has a median particle size of less than about 50 microns with 95% of the particles smaller than about 100 microns; and
   (c) one or more second zeolites coated on a surface of the fiber web, wherein the one or more second zeolites contains between about 0.2% and about 4% zinc by weight, and between about 0.4% and about 4% by weight of one or more metal ions chosen from K, Li, Mg, Ba and Fe, and wherein the one or more second zeolites has a median particle size of less than about 25 microns with 95% of the particles smaller than about 50 microns; and
   wherein the composite is configured as a composting bag.

3. A method of making an odor control composite, the method comprising:
   (a) contacting at least one zeolite with a solution of one or more metal ions, whereby the one or more metal ions diffuses into the zeolite to form at least one ion exchanged zeolite, wherein the at least one ion exchanged zeolite contains between about 0.2% and about 4% Zn by weight, and between about 0.4% and about 4% by weight of one or more metals chosen from K, Li, Mg, Ba and Fe;
   (b) preparing first zeolite particles of at least one ion exchanged zeolite having a median particle size of less than about 50 microns with 95% of the particles smaller than about 100 microns;
   (c) contacting fibers with a liquid to form a slurry;
   (d) incorporating the first zeolite particles into the fiber slurry;
   (e) forming a fiber web from the slurry;
   (f) preparing second zeolite particles of at least one ion exchanged zeolite having a median particle size of less than about 25 microns with about 95% of the particles smaller than about 50 microns;
   (g) applying the second zeolite particles to one or more surfaces of the fiber web; and
   (f) forming the fiber web into a cover for a landfill.

4. A method of making an odor control composite, the method comprising:
   (a) contacting at least one zeolite with a solution of one or more metal ions, whereby the one or more metal ions diffuses into the zeolite to form at least one ion exchanged zeolite, wherein the at least one ion exchanged zeolite contains between about 0.2% and about 4% Zn by weight, and between about 0.4% and about 4% by weight of one or more metals chosen from K, Li, Mg, Ba and Fe;
   (b) preparing first zeolite particles of at least one ion exchanged zeolite having a median particle size of less than about 50 microns with 95% of the particles smaller than about 100 microns;
   (c) contacting fibers with a liquid to form a slurry;
   (d) incorporating the first zeolite particles into the fiber slurry;
   (e) forming a fiber web from the slurry;
   (f) preparing second zeolite particles of at least one ion exchanged zeolite having a median particle size of less than about 25 microns with about 95% of the particles smaller than about 50 microns;
   (g) applying the second zeolite particles to one or more surfaces of the fiber web; and
   (f) further comprising forming the fiber web into a compost bag.

5. A method of controlling odor from a landfill, the method comprising covering at least a portion of the landfill with a cover comprising an odor control composite, the odor control composite comprising:

(a) a fiber web; and (b) one or more zeolites containing between about 0.2% and about 4% Zn by weight, and between about 0.4% and about 4% by weight of one or more metals chosen from K, Li, Mg, Ba and Fe, wherein the odor control composite has a weight per unit area between about 30 g/m$^2$ and about 250 g/m$^2$ and a tensile strength between about 10 Nm/g and about 200 Nm/g.

6. The method of claim 5, wherein covering at least a portion of the landfill comprises providing the cover in the form of a roll having a width of at least about 36 inches and a diameter of at least about 24 inches, and unrolling the roll over an exposed surface of a landfill.

7. The method of claim 5, further comprising ballasting the cover.

8. The method of claim 7, wherein ballasting comprises placing waste derived ballast, sand, boiler ash, or ground organic matter on the unrolled cover.

9. The method of claim 7, wherein ballasting comprises placing weights on a surface of the cover as it is unrolled.

10. The method of claim 5, wherein the odor control composite comprises a paper product.

11. The method of claim 3, wherein the cover is an alternative daily cover.

12. The method of claim 5, wherein the cover is an alternative daily cover.

13. The method of claim 6, wherein the cover is an alternative daily cover.

14. The method of claim 7, wherein the cover is an alternative daily cover.

15. The method of claim 8, wherein the cover is an alternative daily cover.

16. The method of claim 9, wherein the cover is an alternative daily cover.

17. The method of claim 10, wherein the cover is an alternative daily cover.

* * * * *